United States Patent [19]

Vogel

[11] Patent Number: 4,491,581

[45] Date of Patent: Jan. 1, 1985

[54] 4-(2,1,3-BENZOXADIAZOL-4-YL)-1,4-DIHYDROPYRIDAZINE DERIVATIVES, THEIR PRODUCTION AND PHARMACEUTICAL COMPOSITIONS

[75] Inventor: Arnold Vogel, Riehen, Switzerland

[73] Assignee: Sandoz Ltd., Basle, Switzerland

[21] Appl. No.: 437,280

[22] Filed: Oct. 28, 1982

[30] Foreign Application Priority Data

Nov. 3, 1981 [CH] Switzerland .................. 7023/81

[51] Int. Cl.³ .................. A61K 31/50; C07D 413/10
[52] U.S. Cl. .................. 424/250; 544/238; 548/126
[58] Field of Search .................. 544/238; 424/250

[56] References Cited

U.S. PATENT DOCUMENTS 3,920,646 11/1975 Houlihan .................. 544/238

*Primary Examiner*—Glennon H. Hollrah
*Assistant Examiner*—James H. Turnipseed
*Attorney, Agent, or Firm*—Gerald D. Sharkin; Robert S. Honor; Joseph J. Borovian

[57] ABSTRACT

Novel 4-(2,1,3-benzoxadiazol-4-yl)-1,4-dihydropyridazines, particularly compounds of the formula I,

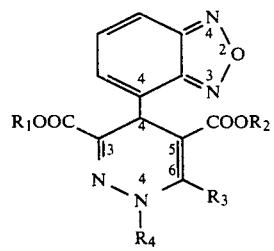

wherein
$COOR_1$ and $COOR_2$ are the same or different carboxylic acid ester groups,
$R_3$ is H or $(C_{1-6})$alkyl and
$R_4$ is H, $(C_{1-6})$alkyl, $(C_{3-6})$alkenyl or -alkynyl, $(C_{3-7})$cycloalkyl, $(C_{4-8})$cycloalkylalkyl, $(C_{7-9})$phenylalkyl or $(C_{9-12})$ phenylalkenyl, the phenyl ring being unsubstituted or mono-, di- or trisubstituted independently by halogen, OH, $(C_{1-4})$alkyl or -alkoxy, for the treatment of coronary insufficiency, spasms in smooth muscles, hypertension or cerebrovascular insufficiency.

7 Claims, No Drawings

4-(2,1,3-BENZOXADIAZOL-4-YL)-1,4-DIHYDROPYRIDAZINE DERIVATIVES, THEIR PRODUCTION AND PHARMACEUTICAL COMPOSITIONS

This invention relates to novel 4-(2,1,3-benzoxadiazol-4-yl)-1,4-dihydropyridazine derivatives, their production and their pharmaceutical compositions.

We have found that 4-(2,1,3-benzoxadiazol-4-yl)-1,4-dihydropyridazines, which may be optionally substituted in any available position, especially those encompassed by the following formula I, possess interesting pharmacological activity.

The present invention provides 4-(2,1,3-benzoxadiazol-4-yl)-1,4-dihydropyridazines, hereinafter referred to as compounds of the invention.

The present invention provides particularly compounds of formula I

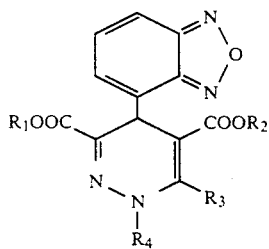

wherein
COOR$_1$ and COOR$_2$ are the same or different carboxylic ester groups
R$_3$ is H or (C$_{1-6}$)alkyl
R$_4$ is H, (C$_{1-6}$)alkyl, (C$_{3-6}$)alkenyl or -alkynyl, (C$_{3-7}$)-cycloalkyl, (C$_{4-8}$)cycloalkylalkyl, (C$_{7-9}$)phenylalkyl or (C$_{9-12}$)phenylalkenyl, the phenyl ring being unsubstituted or mono-, di- or trisubstituted independently by halogen, OH, (C$_{1-4}$)alkyl or -alkoxy.

In a group of compounds of formula I R$_1$ and R$_2$ are preferably independently (C$_{1-12}$)alkyl, (C$_{3-6}$)alkenyl or -alkynyl, (C$_{3-7}$)cycloalkyl, (C$_{4-8}$)cycloalkylalkyl, (C$_{3-12}$)alkoxyalkyl, (C$_{3-12}$)alkylthioalkyl, (C$_{2-6}$)hydroxyalkyl, (C$_{4-8}$)hydroxyalkoxyalkyl, phenyl or (C$_{7-10}$)phenylalkyl and R$_3$ and R$_4$ are as defined above.

In another group of compounds of formula I COOR$_1$ and COOR$_2$ are preferably the same or different carboxylic ester groups, R$_3$ is (C$_{1-6}$)alkyl and R$_4$ is H or (C$_{1-6}$)alkyl.

In these groups R$_1$ and R$_2$ are especially independently (C$_{1-12}$) alkyl.

In the compounds of formula I R$_1$ is preferably (C$_{1-4}$)alkyl and/or R$_2$ is preferaby (C$_{1-4}$)alkyl and/or R$_3$ is preferably methyl and/or R$_4$ is preferably H or methyl.

The present invention also provides a process for the production of a 4-(2,1,3-benzoxadiazol-4-yl)-1,4-dihydropyridazine which comprises
(a) reacting a 3-(2,1,3-benzoxadiazol-4-yl)-4-nitrobutyraldehyde alkali metal or ammonium salt with ozone and a hydrazine, or
(b) producing a 4-(2,1,3-benzoxadiazol-4-yl)-1,4-dihydro-3-pyridazine substituted in the 1 position of the pyridazine ring by alkylating the corresponding compound unsubstituted in the 1 position, and if required converting the resulting 4-(2,1,3-benzoxadiazol-4-yl)-1,4-dihydropyridazine into another 4-(2,1,3-benzoxadiazol-4-yl)-1,4-dihydropyridazine.

The present invention in another aspect provides a process for the production of a compound of the invention, which includes the step of
(a) reacting a compound of formula II

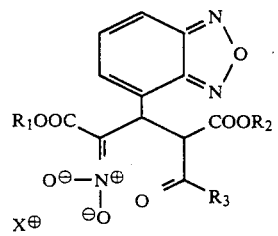

wherein R$_1$, R$_2$ and R$_3$ are as defined above and X$^\oplus$ is an alkali metal ion or an ammonium ion, with ozone and with a hydrazine of formula

R$_4$-NH-NH$_2$ wherein R$_4$ is as defined above or
(b) preparing compounds of formula Ia

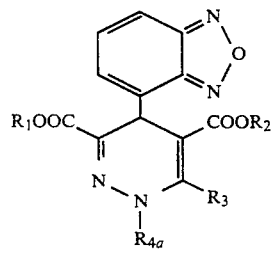

wherein
R$_1$, R$_2$ and R$_3$ are as defined above and
R$_{4a}$ is (C$_{1-6}$)alkyl, (C$_{3-6}$)alkenyl or -alkynyl, (C$_{3-7}$)cycloalkyl, (C$_{4-8}$)cycloalkylalkyl, (C$_{7-9}$)phenylalkyl or (C$_{9-12}$)phenylalkenyl, the phenyl ring being unsubstituted or mono-, di- or trisubstituted independently by halogen, OH, (C$_{1-4}$)alkyl or -alkoxy by alkylating a compound of formula Ib

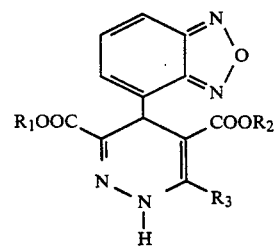

wherein R$_1$, R$_2$ and R$_3$ are as defined above.

In process (a) the ozonolysis may be carried out in an inert solvent, particularly an alcohol such as methanol, at a low temperature, preferably at approximately $-70°$ C., in a manner analogous to that described in J. Org. Chem. 39, 259(1974). The reaction with the hydrazine may subsequently be effected at temperatures of approximately $-20°$ C. to the reflux temperature of the solvent.

Process (b) may be performed in an inert solvent, such as dimethyl sulphoxide or dimethyl formamide, at approximately room temperature. The alkylation agent may be a reactive ester of a hydrohalic acid or sulphuric acid or sulphonic acid.

The compounds of formula I can be isolated and purified in known manner.

The compounds of formula II may be produced by an addition reaction of suitable salts of 3-oxocarboxylic esters of formula III

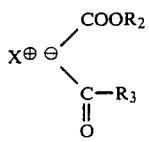

to compounds of formula IV

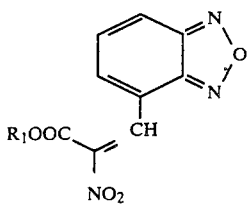

wherein $R_1$, $R_2$ and $R_3$ are as defined above.

The compounds of formula IV may be obtained by condensation of 2,1,3-benzoxadiazol-4-yl-carboxaldehyde with nitro-acetic esters, preferably in benzene, whilst catalyzing the reaction with piperidine and acetic acid [A. R. Surrey, H. F. Hammer and C. M. Suter, J. Am. Chem. Soc. 66, 1933 (1944)] or particularly by the method of W. Lehnert with titanium tetrachloride and N-methylmorpholine in tetrahydrofuran [Tetrahedron 28, 663 (1972)].

Starting materials for other 4-(2,1,3-benzoxadiazol-4-yl)-1,4-dihydropyridazines may be produced in analogous manner to that described above.

In the following Examples all temperatures are in degrees Centigrade and are uncorrected.

EXAMPLE 1

4-(2,1,3-benzoxadiazol-4-yl)-1,4-dihydro-5-isopropoxycarbonyl-6-methyl-3-pyridazine carboxylic acid methylester (I $R_4$=H, $R_3$=CH$_3$, $R_1$=CH$_3$, $R_2$=isopropyl), (Process a))

(a)
3-(2,1,3-benzoxadiazol-4-yl)-4-isopropoxycarbonyl-2-nitro-5-oxo-hexanoic acid methylester A solution of 5.7 g of 3-(2,1,3-benzoxadiazol-4-yl)-2-nitro-propenoic acid methylester (IV,$R_1$=CH$_3$) in 120 ml of dioxane is added to 4.2 g of the dry sodium salt of acetoacetic acid isopropylester. The suspension is stirred for 3 hours at room temperature. The mixture is poured into 120 ml of ice water and shaken with ether. The aqueous phase is acidified with hydrochloric acid whilst cooling, and extracted with methylene chloride. The methylene chloride solution is dried over magnesium sulphate and the solvent is evaporated under vacuum, after which the substance is obtained.

(b)
3-(2,1,3-benzoxadiazol-4-yl)-4-isopropoxycarbonyl-2-nitro-5-oxo-hexanoic acid methylester-Na salt A solution of 16.46 g of 3-(2,1,3-benzoxadiazol-4-yl)-4-isopropoxycarbonyl-b 2-nitro-5-oxo-hexanoic acid methylester in 200 ml of methanol is added dropwise at 0° to the solution of 0.96 g of sodium in 100 ml of methanol. The resulting salt solution is used in the following step without isolating and purifying the salt.

(c)
4-(2,1,3-benzoxadiazol-4-yl)-1,4-dihydro-5-isopropoxycarbonyl-6-methyl-3-pyridazine-carboxylic acid methylester An excess of dry ozone is passed at −78° through the reaction mixture produced as under (b). After removing the excess ozone with nitrogen, 2.5 ml of hydrazine hydrate are added at −20° and the solution is heated for 10 hours at reflux temperature of the solvent. The solution is then evaporated under vacuum, and the residue shaken with ice water and methylene chloride. The methylene chloride solution is dried over magnesium sulphate and the solvent is evaporated under vacuum. The crude product is purified by chromatography on silica gel with methylene chloride - ether mixtures as the eluants, and the substance obtained is crystallized from ether. m.p. 178°.

The following compounds of formula I are produced in a manner analogous to that of Example 1:

FORMULA I

| Ex. | $R_4$ | $R_3$ | $R_1$ | $R_2$ | M.p. |
|-----|-------|-------|-------|-------|------|
| 2 | H | CH$_3$ | C$_2$H$_5$ | C$_2$H$_5$ | 168° |
| 3 | H | CH$_3$ | isopropyl | CH$_3$ | 160° |

EXAMPLE 4:

4-(2,1,3-benzoxadiazol-4-yl)-1,4-dihydro-5-isopropoxycarbonyl-1,6-dimethyl-3-pyridazine carboxylic acid methylester (I $R_4$=$R_3$=CH$_3$,$R_1$=CH$_3$, $R_2$=isopropyl), [Process (b)]

To the solution of 3.2 g of 4-(2,1,3-benzoxadiazol-4-yl)-1,4-dihydro-5-isopropoxycarbonyl-6-methyl-3-pyridazine carboxylic acid methylester (I $R_4$=H, $R_3$=CH$_3$, $R_1$=CH$_3$, $R_2$=isopropyl) in 60 ml of dimethyl sulphoxide are added 2.0 g of powdered potassium hydroxide, and then 1.1 ml of methyl iodide are dropwise added. The mixture is stirred for 45 minutes at room temperature, and is then poured into 120 ml of ice water and extracted with methylene chloride. The product obtained after drying the methylene chloride solution over magnesium sulphate and evaporating under vacuum is purified by chromatography on silica gel. After elution with methylene chloride - ether mixtures and subsequent crystallization from ether - petroleum ether, the pure substance is obtained with a m.p. of 107°.

In an analogous manner the following compounds of formula I may be prepared:

| Ex. | $R_1$ | $R_2$ | $R_3$ | $R_4$ |
|-----|-------|-------|-------|-------|
| A | n-decyl | n-pentenyl-3 | H | n-hexyl |
| B | n-octyl | n-propenyl-2 | i-pentyl | n-pentenyl-3 |
| C | phenyl | cyclopentyl | n-hexyl | n-hexynyl-3 |
| D | benzyl | cyclohexylmethyl | methyl | cyclohexyl |
| E | n-hexyl | n-octyloxyethyl | ethyl | cyclohexylethyl |
| F | i-propyl | i-propylthiobutyl | ethyl | phenylethyl |
| G | n-propyl | hydroxypentyl | propyl | phenylpropenyl-2 |

-continued

| Ex. | R₁ | R₂ | R₃ | R₄ |
|---|---|---|---|---|
| H | i-butyl | hydroxymethoxy-propyl | methyl | 2,3-dimethoxy-benzyl |

The compounds of the invention are useful, because they possess pharmacological activity in animals and are therefore of use as pharmaceuticals.

In particular they lead to a dilatation of the coronary vessels as indicated in tests measuring the blood flow to the myocardium of an anaesthetized cat by means of the microsphere method [A. M. Rudolph and M. S. Heymann: Circular Research 21, 163 (1967), modified by R. P. Hof, F. Wyler and G. Stalder, Basic Res. Cardiol. 75, 747-756 (1980)] after administration of from 10 to 100 µg/kg i.v. or 30 to 1000 µg/kg i.d. of the active substance.

The compounds are therefore useful in the treatment of coronary insufficiency, e.g. angina pectoris.

The compounds of the invention exhibit calcium antagonistic activity as indicated in standard tests, e.g. by an inhibition of a calcium induced contraction of isolated strips of the rabbit aorta, suspended in a depolarizing solution at concentrations of $10^{-9}$ to $10^{-5}$ M of the active substances (modified method of Godfraind and Kaba, Brit. J. Pharm. 36, 549-560 (1969)).

The compounds are therefore useful in the treatment of spasms in smooth muscles.

The compounds of the invention have antihypertensive activity, as indicated in standard tests by a reduction in the blood pressure.

For example, the compounds have a blood pressure reducing effect on the normotensive narcotized cat upon i.v. administration of from 10 to 300 µg/kg animal body weight.

The compounds are therefore useful in the treatment of hypertension.

Additionally the compounds of the invention lead to an increase of the cerebral blood flow as indicated in the above mentioned microsphere method on the anaesthetized cat upon administration of from 10 to 100 µg/kg i.v. of the compounds.

The compounds are therefore useful in the treatment of cerebrovascular insufficiency, such as cerebrovascular spasms, or insults, e.g. stroke.

For these uses the dosage will, of course, vary depending on the compound employed, mode of administration and therapy desired. However, in general, satisfactory results are obtained with a daily dosage of from about 0.01 to about 12 mg/kg animal body weight, conveniently given in divided dosages 2 to 4 times a day or in sustained release form.

For the larger mammal, the total daily dosage is in the range from about 10 to about 500 mg and dosage forms suitable for oral administration compose from about 2.5 to about 250 mg of the compounds, admixed with a solid or liquid pharmaceutical carrier or diluent.

An example of a daily dosage for larger mammals is from 20 to 100 mg for the compound of Example 1.

The preferred indications are the treatment of angina pectoris and hypertension, especially angina pectoris. The compound of Example 1 is the preferred compound.

The compounds of the invention may be administered in similar manner to known standards for use for the above indications. The suitable daily dosage for a particular compound will depend on a number of factors such as its relative potency and the duration of the activity.

The compound of Example 1 exhibits in the above mentioned anaesthetized cat an increase in the blood flow to the myocardium of the order of 160% on administration of 10 µg/kg i.v.

The compound of Example 1 is 3 to 4 times more potent than Nifedipine in this test.

It is therefore indicated that the compound may be administered at three times lower dosages than the standard compound. The duration of the activity is for the compound of Example 1 2 hours after administration of 10 µg/kg i.v.

A compound of formula I may be administered in free base form. The present invention also provides a pharmaceutical composition comprising a compound of the invention in association with a pharmaceutical carrier or diluent. Such composition may be prepared by conventional techniques to be in conventional forms, for example, capsules or tablets.

I claim:

1. A compound of the formula

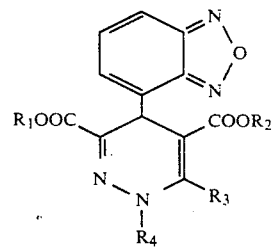

wherein

R₁ and R₂ are, independently, (C₁₋₁₂)alkyl, (C₃₋₆)alkenyl, (C₃₋₆)alkynyl, (C₃₋₇) cycloalkyl, (C₄₋₈)-cycloalkylalkyl, (C₃₋₁₂)alkoxyalkyl, (C₃₋₁₂)alkylthioalkyl, (C₂₋₆)hydroxyalkyl, (C₄₋₈)hydroxyalkoxyalkyl, phenyl or (C₇₋₁₀)phenylalkyl;

R₃ is hydrogen or (C₁₋₆)alkyl; and

R₄ is hydrogen, (C₁₋₆)alkyl, (C₃₋₆)alkenyl, (C₃₋₆)alkynyl, (C₃₋₇)cycloalkyl, (C₄₋₈)cycloalkylalkyl, (C₇₋₉)phenylalkyl or (C₉₋₁₂)phenylalkenyl, the phenyl ring being unsubstituted or mono-, di- or trisubstituted independently by halo, hydroxy, (C₁₋₄)alkyl or (C₁₋₄)alkoxy.

2. A compound of claim 1 wherein R₁ and R₂ are, independently, (C₁₋₁₂) alkyl, R₃ is (C₁₋₆)alkyl and R₄ is hydrogen or (C₁₋₆)alkyl.

3. A compound of claim 1 wherein R₃ is (C₁₋₆)alkyl and R₄ is hydrogen or (C₁₋₆)alkyl.

4. A compound of claim 1 selected from the group consisting of 4-(2,1,3-benzoxadiazol-4-yl)-1,4-dihydro-5-isopropoxycarbonyl-1,6-dimethyl-3-pyridazine carboxylic acid methylester, 4-(2,1,3-benzoxadiazol-4-yl)-1,4-dihydro-5-ethyoxycarbonyl-6-methyl-3-pyridazine carboxylic acid ethylester and 4-(2,1,3-benzoxadiazol-4-yl)-1,4-dihydro-5-methoxycarbonyl-6-methyl-3-pyridazine carboxylic acid isopropylester.

5. 4-(2,1,3-benzoxadiazol-4-yl)-1,4-dihydro-5-isopropoxycarbonyl-6-methyl-3-pyridazine carboxylic acid methylester.

6. A pharmaceutical composition useful in treating coronary insufficiency, spasms in smooth muscles, hypertension or cerebrovascular insufficiency comprising a pharmaceutically acceptable carrier or diluent and a therapeutically effective amount of a compound of claim 1.

7. A method of treating coronary insufficiency which comprises administering a therapeutically effective amount of a compound of claim 1 to a subject in need of such treatment.

* * * * *